United States Patent [19]

Wang

[11] Patent Number: 5,124,020
[45] Date of Patent: Jun. 23, 1992

[54] ADJUSTABLE HEIGHT AND WIDTH APERTURE FOR CAPILLARY PHOTODETECTOR CELL

[75] Inventor: Tiansong Wang, Piscataway, N.J.

[73] Assignee: Rutgers, The State University, New Brunswick, N.J.

[21] Appl. No.: 412,425

[22] Filed: Sep. 26, 1989

[51] Int. Cl.$^5$ .................. G01N 27/26; B01D 57/02
[52] U.S. Cl. ........................ 204/299 R; 204/180.1
[58] Field of Search ............... 204/299 R, 180.1; 356/271, 266, 233; 350/319

[56] References Cited

U.S. PATENT DOCUMENTS

| | | | |
|---|---|---|---|
| 2,998,730 | 9/1961 | Raskhodoff et al. | 350/271 |
| 3,537,777 | 11/1970 | Flynn | 350/271 |
| 3,684,386 | 8/1972 | Noll | 350/271 X |
| 4,006,990 | 2/1977 | Munk | 356/440 X |
| 4,618,260 | 11/1986 | Okubo | 356/334 X |
| 4,854,700 | 8/1989 | Cutie et al. | 356/410 X |

FOREIGN PATENT DOCUMENTS 3306763 9/1983 Fed. Rep. of Germany .

OTHER PUBLICATIONS

Wang, Tiansong; Hartwick, Richard A; Champlin, Paul B. "Adjustable aperture-width detector cell for on-column detection in capillary zone electrophoresis" Journal of Chromatography 462 (1989) 147-54.

*Primary Examiner*—John Niebling
*Assistant Examiner*—John S. Starsiak, Jr.
*Attorney, Agent, or Firm*—Lerner, David, Littenberg, Krumholz & Mentlik

[57] ABSTRACT

Adjustable aperture for photoelectric monitoring of a light transmitted through a capillary, wherein the aperture includes a device for providing a light beam having a predetermined limited extent in a vertical direction, a selectively operable device for limiting the extent of the light beam in a horizontal direction transverse to the vertical direction so that the extent in the horizontal direction can be selectively varied, and a device for positioning a capillary having longitudinal and diametral directions so that the diametral direction of the capillary lies in the vertical direction of the light beam and so that the beam of light passes through the capillary in a diametral dimensional thereof. The adjustable aperture can be used in combination with capillary zone electrophoresis and high performance liquid chromatography apparatus. Methods are provided for analyzing samples of one or more compounds by capillary zone electrophoresis or high performance liquid chromatography using the adjustable aperture.

12 Claims, 2 Drawing Sheets

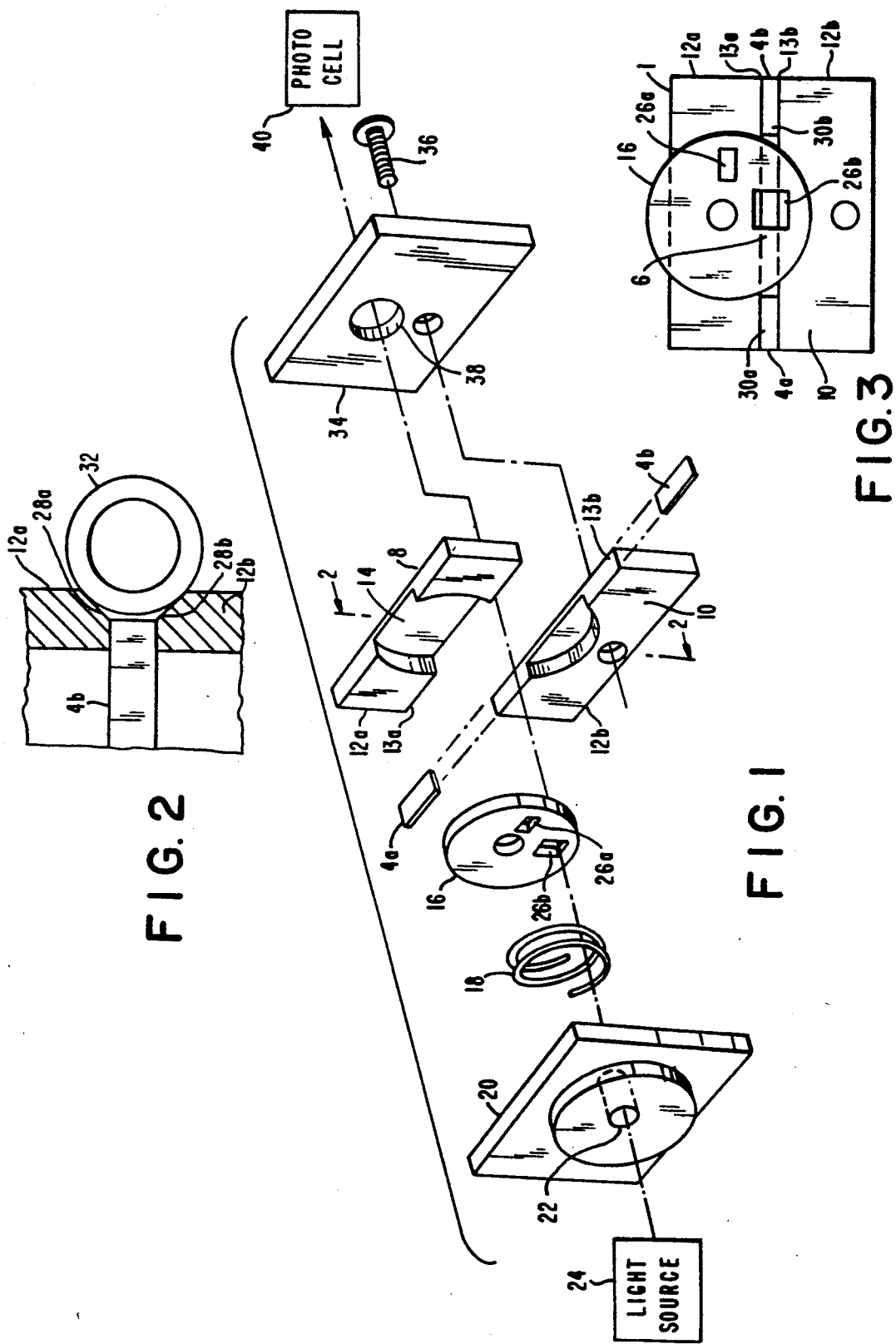

ADJUSTABLE HEIGHT AND WIDTH APERTURE FOR CAPILLARY PHOTODETECTOR CELL

BACKGROUND OF THE INVENTION

The present invention relates to adjustable height and width apertures for on-column capillary detector cells used for capillary methods of separation, and in particular to adjustable height and width apertures for on-column photo-detector cells for capillary zone electrophoresis (CZE), also known as high-performance capillary electrophoresis (HPCE).

Electrophoresis is a separation technique in which the fractionation of the components of a mixture is achieved by the migration of the components through a solution under the influence of an electric field. The individual components move through the solution at varying rates in response to the electric field's influence. The differences in migration rates are generally a function of the charge and volume of a component. Electrophoresis is the dominant separation method used in the study of DNA, proteins and other biological substances.

Similar to chromatography, the term "theoretical plate number" is used to describe the separation efficiency of electrophoresis. As the number of theoretical plates a mixture passes through increases, the degree of separation of the mixture's components consequently increases. As the number of theoretical plates a mixture passes through over a unit period of time increases, the rate of separation of the mixture's components consequently increases.

CZE is a recently developed form of electrophoresis in which a sample solution is introduced into a fine tube (50–75 micron inside diameter) filled with a buffered liquid with separation occurring as a result of the differential movement of sample components toward one of two electrodes by which an electric field is applied to the contents of the tube. Some major problems relative to electrophoresis methods, such as dissipation of heat and suppression of convection, have been greatly improved by using fine capillary tubes. CZE can generate $10^5$ to $10^6$ theoretical plates within 30 minutes. This separation technique has been successfully applied to analyze a variety of samples including proteins, amino acids, nucleosides, inorganic ions and neutral molecules.

Until the present invention, suitable means for detecting sample components resolved by CZE have not been well developed. The problem is that for a typical CZE peak having a retention time of 500 seconds and 250,000 theoretical plates, the peak width is four seconds. In a capillary with a 50 micron inside diameter and a linear velocity of one mm per second, four seconds corresponds to only eight nanoliters in volume. Stated another way, CZE requires the detection of a series of segments of separated sample components occupying at best 4 mm long segments of the capillary so that the sample volumes to be tested for the presence of the component is at best several nanoliters. Making matters more difficult, the segments will only be separated by one mm or even less and the series of separated sample component segments will be passing through the capillary at a rate of one mm a second. To prevent overlap in the detection of the segments, a detector cell is required having small volume and high sensitivity.

On-column detectors have been used to meet these requirements, employing fluorescent, electrochemical, ultraviolet (UV) and visible (VIS) absorption spectrophotometric detection methods, such as those methods disclosed in Walbroehl et al., *J. Chromatogr.*, 315, 135 (1984) and Terabe et al., *Anal. Chem.*, 56, 111 (1984). UV detectors, though less sensitive than fluorescence detectors, are still the most widely used because of their relative versatility. A section of the capillary downstream of the region where separation occurs is passed through a spectrophotometer detector cell. Light is transmitted through the capillary, and the sample component is identified by its characteristic absorption pattern.

While it has been possible in the past to construct on-column UV detector cells, the prior art was not successful when reducing cell volume to maintain detector sensitivity. This occurs when a light beam having a thickness dimension greater than the inside diameter of the capillary is transmitted through the capillary. The light passing outside of the inner diameter of a capillary creates a high background and drowns out the absorption signal.

Moreover, the prior art did not set a reasonable width of the light beam to avoid overlap in the detection of component segments. Such designs are: Yang, *J. High Resolut. Chromatogr Chromatogr. Commun.*, 4, 83 (1981), which discloses an on-column UV detector constructed by stripping the polymer coating of a capillary and placing the capillary in the light path of a detector. Terabe et al., *Anal. Chem., id.*, disclose a UV detector with a 0.05 by 0.75 mm slit. Walbroehl et al., *J. Chromatogr., id.*, disclose a 100 micron pinhole as the aperture of a UV detector cell. Spino et al., *J. Lig. Chromatogr.*, 10, 1603 (1987) disclose a detector cell fabricated by glueing a capillary and two razor blades onto a cell block, producing an aperture about 6 mm by the capillary inner diameter. Kientz et al., *J. High Resolut. Chromatogr. Chromatogr. Comm.*, 11, 294 (1988) disclose a cell aperture made by drilling a 0.4 mm diameter hole in the outer holder of the capillary. Foret et al., *Electrophoresis*, 7, 430 (1986) disclose an on-column detector fabricated from optical fibers. None of the disclosed devices use aperture dimensions that maximize signal to noise ratio and at the same time prevent overlap in the detection of separated sample components.

Optimum detector performance is a function of three important aspects of the design of on-column UV detector cell apertures for CZE. First, light should only pass through the inner diameter of the capillary. When a large amount of light passes through the rim of the capillary, the signal becomes very sensitive to the refractive index changes of the solution as well as the distance between the capillary and the photodetector, and the signal to noise ratio and linear range of detection will be reduced. Second, the dimension of the aperture corresponding to the portion of the capillary segment selected for detection should be minimized to prevent overlap in the detection of separated component segments and should be adjustable to meet different detection requirements that vary with the samples to be separated. Finally, installation and removal of capillaries should be convenient and accurate.

A photodetector cell aperture capable of meeting these requirements would be highly desirable.

SUMMARY OF THE INVENTION

The above requirements are addressed by the present invention.

One aspect of the present invention provides an adjustable aperture for photoelectric monitoring of light transmitted through a capillary. The adjustable aperture combines a means for providing a beam of light having a predetermined limited extent in a vertical direction with a selectively operable means for limiting the extent of the light beam in a horizontal direction transverse to the vertical direction so that the extent of the light beam in the horizontal direction can be varied, and a means for positioning a capillary having longitudinal and diametral directions so that a diametral direction of the capillary lies in the vertical direction of the light beam and so that the light beam passes through the capillary in a diametral direction thereof.

In preferred embodiments of the present invention, the means for providing a beam of light having a limited extent in a vertical direction is capable of providing a beam of light having a limited extent in a vertical direction between about 10 and about 100 microns. In more preferred embodiments of the present invention, the diametral direction of the capillary includes an inner diametral dimension and the means for providing a beam of light having a limited extent in a vertical direction is capable of providing a beam of light having a limited extent in the vertical direction less than the inner diametral dimension of the capillary.

Another aspect of the present invention provides the adjustable aperture of the present invention in combination with a capillary zone electrophoresis apparatus or a high performance liquid chromatography apparatus.

In still yet another aspect of the present invention, methods are provided for analyzing samples containing one or more compound by capillary zone electrophoresis or high performance liquid chromatography using capillary devices having photodetectors with adjustable apertures which are adjusted so as to maximize the resolution or the sensitivity of the photodetector with respect to the sample components.

Other objects, features and advantages of the present invention will be more readily apparent from the detailed description of the preferred embodiments set forth below taken in conjunction with the accompanying drawings.

BRIEF DESCRIPTION OF THE DRAWINGS

FIG. 1 is a schematic exploded view of an adjustable width aperture according to one embodiment of the invention.

FIG. 2 is an enlarged fragmentary sectional view taken along lines 2—2 of FIG. 1.

FIG. 3 is a rear elevational view of the adjustable width aperture depicted in FIG. 1, without the spring or base member.

DETAILED DESCRIPTION OF THE PREFERRED EMBODIMENT

Figure 4:
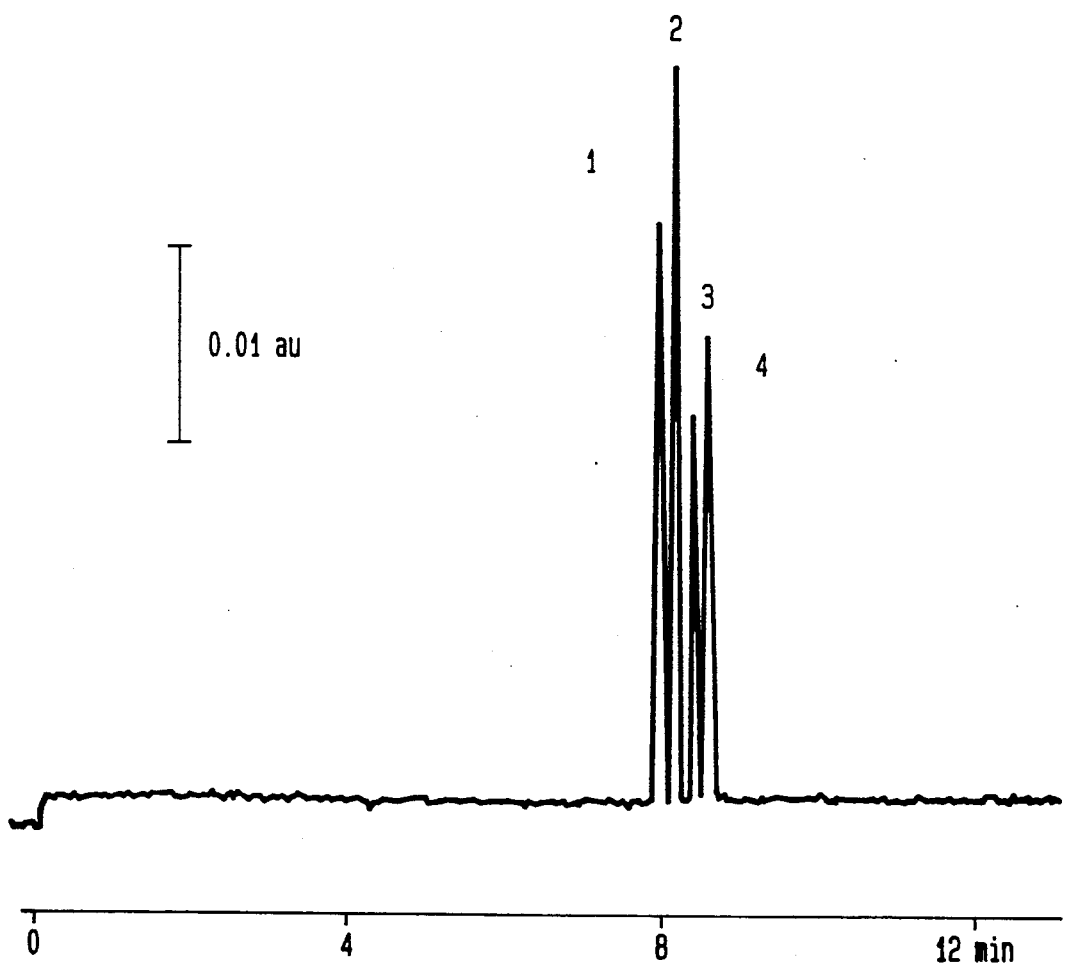
FIG. 4 is a graph depicting the separation of four nucleosides by CZE as detected by a UV detector using an adjustable-width aperture of the present invention.

The adjustable-width aperture of the present invention can be used with photocell detector systems for any method of capillary separation, including, but not limited to High Performance Liquid Chromatography (HPLC) and Capillary Zone Electrophoresis (CZE). As used in this disclosure, the term "light" refers broadly to radiation in the infrared and ultraviolet regions of the electromagnetic spectrum, as well as to visible light. The portion of the electromagnetic spectrum selected for detection is that portion convenient for the identification of the materials to be separated by the capillary. The photocell selected for use with the invention will be responsive to that portion of the electromagnetic spectrum to be detected. For materials conventionally separated by HPLC and CZE, the ultraviolet portion, the visible portion, and the combined ultraviolet-visible portion of the electromagnetic spectrum typically are used to detect and identify such materials.

Referring to FIGS. 1 and 3, an adjustable height and width aperture according to one embodiment of the present invention has an aperture body 1 formed from metal plates 12a and 12b having confronting sides 13a and 13b spaced apart by shims 4a and 4b with an opening 6 between the two shims. The aperture body has a front face 8 and a rear face 10. The rear face has a circular depression 14, in which is situated a washer 16 and spring 18. A base member 20 is affixed to the rear face of the aperture body, retaining the washer and spring in the circular depression. The base member has a channel 22 in alignment with the aperture body opening to permit the passage of light therethrough from light source 24. The spring has an open interior that also permits light to pass to the aperture body opening.

The washer is provided with a plurality of slits 26a and 26b of differing width. As shown in FIG. 2, the confronting sides of the metal plates have bevels 28a and 28b along the front face of the aperture body including the aperture body opening. The front face to rear face dimension of the metal plates is thicker than that of the shims between the plates so that the beveled confronting sides of the metal plates in combination with the shims forms V-shaped grooves 30a and 30b on the front face of the aperture body on opposite sides of the aperture body opening 6. Capillary 32 is positioned in the V-shaped grooves and held in place by capillary retainer 34, which is fastened to the aperture body by screw 36. The capillary retainer has an opening 38 in alignment with the aperture body opening and of sufficient width to permit the beam of light emerging from the capillary to pass undisturbed to photocell detector 40.

The circular depression is positioned on the rear face of the aperture body and the edge of the washer protrudes from the side of the aperture body and is rotatable in the depression on the spring. The position of the circular depression also fixes the location of the washer so that each washer slit is capable of alignment with the aperture body opening by rotation of the washer. This arrangement permits interchangeability of the washer slits by rotation of the washer.

The washer with slits serves as a selectively operable means for limiting the extent of a beam of light in a horizontal direction. Beams having a horizontal extent between about 0.2 and about 2.0 mm are preferred. Accordingly, the narrowest slit 26 may be about 0.2 mm wide, whereas the widest slit 26 may be about 2.0 mm wide. Shorter horizontal dimensions are used when maximum resolution is desired. Broader horizontal dimensions are used when greater sensitivity is desired.

The capillary positioned in the V-shaped grooves has a longitudinal direction and diametral directions transverse to the longitudinal direction. The capillary has inner diametral dimensions defined by the inner wall surface of the capillary. The body opening 6 has a vertical dimension defined by the distance between the confronting sides 13a and 13b of the metal plates defined by the thickness of the two shims 4a and 4b, and a horizontal dimension defined by the distance between the two shims 4a and 4b. The vertical dimension of the body opening 6 defined by the thickness of the two shims 4a and 4b is typically between about 10 and 100 microns. More preferably, the vertical dimension of the body opening 6 defined by the thickness of the two shims 4a and 4b is less than the inner diametral dimension of the capillary. The V-shaped grooves position the capillary in alignment with body opening 6 so that a diametral direction of the capillary lies in the vertical dimension of the body opening.

The light beam to be detected originates at the light source 24 and passes through the channel in the base member and the spring. The light beam next passes through the washer slit 26b which is in alignment with the aperture body opening. That slit limits the extent of the horizontal direction of the light beam to the width of the slit. The horizontally limited light beam passes through the aperture body opening 6, which limits the extent of the vertical direction of the light beam to the vertical dimension of the aperture body opening. The light beam, the extent of which has been limited horizontally and vertically, then passes through the capillary and the channel and the capillary retainer to the photocell detector.

As used herein, horizontal and vertical direction references are made from the frame of reference of the photocell detector and the capillary separation device to which it is attached and correspond to the longitudinal and diametral directions of the capillary, respectively, which for various reasons may not be strictly aligned with the earth's horizon.

Any means of providing a beam of light having a predetermined limited extent in a vertical direction suitable for use with photodetector cells in capillary separation systems may be used in the present invention. Means of providing a beam of light including a body having a predetermined limited extent in a vertical direction with openings having a vertical dimension that limit the extent in a vertical direction of a beam of light passing therethrough are also preferred, such as the aperture body opening of the aperture body of the depicted embodiment.

Any means suitable for selectively limiting the extent of a beam of light in a horizontal direction suitable for use with photodetection cells for capillary separation systems may be used with the present invention to selectively vary in a horizontal direction the beam of light provided. Of the selectively operable means for limiting the extent of a light beam in a horizontal direction, an element defining a plurality of selectively interchangeable slits of differing horizontal dimensions in combination with means for aligning each slit with the means for providing a beam of light having a predetermined limited extent in a vertical direction are preferred, such as the washer with slits positioned in the circular depression on the rear face of the aperture body of the depicted embodiment.

Other means useful as the selectively operable means for limiting the extent of a light beam in a horizontal direction include a means having a tapered slot moveable relative to the aperture body. Alternatively, the means for limiting the beam may include a pair of bodies and a micrometer adjustment capable of selectively adjusting the horizontal distance between these bodies. Moreover, the rotatable single means defining a plurality of selectively interchangeable slits is preferred because it provides a simple means by which the horizontal dimension of a beam of light can be varied in a set and reproducible manner.

Other means for positioning the capillary may be used in accordance with the present invention. Thus, fasteners, clamps and alignment devices such as positioning markers on the body may be employed, and such alone or in combination. When the means for providing a beam of light having a limited extent in a vertical direction includes a body having an opening with vertical dimensions that limit the extent in a vertical direction of a beam of light passing therethrough, such as the aperture body of the depicted embodiment, preferred capillary positioning means include a groove on the front surface of the body having an opening, the groove being colinear with the horizontal dimension of the opening, and means for retaining the capillary in the groove, such as the grooves in the front surface of the aperture body and the capillary retainer of the depicted embodiment. Even more preferred are beveled grooves, such as the beveled grooves of the depicted embodiment.

The grooved means of the present invention is preferred because it provides a simple means providing accurate alignment of the capillary inside diameter in the path of the light beam in a set and reproducible manner. Moreover, accurate positioning of the capillary relative to the light beam can be provided even without particularly precise or intricate machining of the components. This accurate positioning eliminates as a variable the alignment of the capillary in the paths of the light beams when the results of different sample preparations are compared.

The following examples serve to provide further appreciation of the invention but are not meant in any way to restrict the effective scope of the invention.

EXAMPLES

EXAMPLE 1

The aperture of the present invention was evaluated using a Kratos SF770UV detector (Applied Biosystems, Ramsey, NJ, U.S.A.) by a static method in which a capillary was filled with test solution with no flow or applied voltage. The capillary was 75 micron inner diameter (I.D.) by 195 micron outer diameter (O.D.) fused silica (Polymicro Technology, Phoenix, AZ, U.S.A.). A $3.0 \times 10^{-4}$ M solution of acetophenone in acetonitrile was used to determine signal-to-noise ratio and linear range of detection. The wavelength of detection was 240 nm. The aperture having a 60 micron vertical dimension was set at 0.95 mm horizontal dimension.

Because no commercial cells for CZE or capillary HPLC are currently available with which to compare the performance of the new aperture, a SF770 standard flow cell was used. The capillary was taped on the surface of the SF770 cell and across the aperture (1.0 mm diameter), after which signal-to-noise ratio and linear range of detection were measured.

The signal and noise portions of absorbance measurements for both the cell having the aperture of the invention and the cell having a conventional aperture are depicted in Table I. The absorbance measured is expressed in absorbance units (a.u.), which is a standardized measurement of the intensity of a beam of light. The unit expresses a fraction or multiple of the intensity of a light standard against which the measured light beam is compared. The data indicates that although the noise measured with the cell using the aperture of the invention is 2.5 times higher than that of the cell with the conventional aperture, the signal obtained from the cell using the aperture of the invention is 14.7 times higher, resulting in an overall improvement of signal-to-noise of nearly six-fold.

TABLE I

| Aperture | Signal (a.u.) | Noise (a.u.) | S/N |
|---|---|---|---|
| 60 Micron × 0.95 mm | $2.2 \times 10^{-2}$ | $1.0 \times 10^{-3}$ | 22 |
| 1.0 mm diameter | $1.5 \times 10^{-3}$ | $0.4 \times 10^{-3}$ | 3.7 |

Measurement of the linear range of detection indicates that the upper limit of concentration is about $3 \times 10^{-3}$ M for both cells regardless of aperture dimension. However, the lower limit of concentration is $3 \times 10^{-5}$ M for the cell using the aperture of the present invention, compared to a lower limit of $2 \times 10^{-4}$ M for the cell having a conventional aperture. The aperture of the present invention producing a higher signal-to-noise ratio expands the linear range of detection by one order of magnitude. If detectors with reduced noise were used, the linear range and detection limit could be improved further.

EXAMPLE 2

Refractive index sensitivity of cells using the aperture of the present invention was examined by determining the baseline shift resulting when the capillary was alternatively filled with 100% methanol followed by a 60:40 ratio of methanol and water.

The tests were run as in Example 1, substituting the 100% methanol and the 60:40 methanol-water solution for the acetophenone-acetonitrile solution. Absorbance was measured at 330 nm. Each test was run four times and statistically analyzed. For each run, the capillary was removed and repositioned. The baseline shift results are summarized in Table II. The data in Table II show that the baseline shift is about 0.02 a.u. This relatively large shift is due largely to the long distance (4 cm) between the cell and the photodetector on the SF770, which is known to cause refractive index sensitivity.

TABLE II

| | Absorbance (a.u.) | | | | |
|---|---|---|---|---|---|
| Solution | 1 | 2 | 3 | 4 | x + S.D. |
| Methanol-water | .0244 | .0194 | .0226 | .0256 | .023 ± .0027 |
| Methanol | .0016 | .0031 | .0013 | .0014 | .0019 ± .0008 |
| Baseline Shift | .0228 | .0163 | .0213 | .0242 | .0212 ± .0034 |

Table II shows that the repeatability of absorbance measurement is good, with the maximum difference being 0.0062 a.u. This result indicates that the groove on the aperture of the present invention can reliably position the capillary.

EXAMPLE 3

In order to demonstrate the actual performance of a cell utilizing the aperture of the present invention, a mixture of nucleosides (AMP, CMP, GMP, UMP, 1 mg/ml each) was analyzed by CZE.

The CZE apparatus described by Jorgenson et al., Science, 222, 266 (Washington, D.C. 1986) was constructed using the cell and detector of Example 1. The power supply (0–30 kV) was a model PS/MJ 30P0400-11 (Glassman High Voltage, Whitehouse Station, NJ, U.S.A.). The buffer solution was 0.05 M sodium dodecyl sulfate in a borate-phosphate solution (pH = 7.0). The fused silica capillary was 50 micron I.D. by 355 micron O.D. The total capillary length was 84 cm, while the length from injection end to the detector was 60 cm. The capillary was rinsed with 0.1 M potassium hydroxide (20 min., about 100 microliters), water and the buffer solution respectively, then was conditioned under high voltage for 24 h. The test sample in the same buffer solution was injected at 2.0 kV for 15 seconds. Analysis was at 25 kV and 50 microamps. The aperture width was set at 1.4 mm. The wavelength of detection was 267 nm with a time constant of 0.50 s.

The electropherogram obtained using the cell with the aperture of the invention is depicted in FIG. 4. The separation is quite good, with peak 1 representing GMP, peak 2 representing AMP, peak 3 representing CMP and peak 4 representing UMP. The column efficiency calculated from the UMP peak is 65,000 theoretical plates (10% peak height).

The invention being thus described, it will be obvious that the same can be varied in many ways. Such variations are not to be regarded as a departure from the spirit and scope of the invention, and all such modifications are intended to be included within the scope of the following claims.

I claim:

1. An adjustable aperture for photoelectric monitoring of light transmitted through a capillary, said aperture comprising:
   (a) means for providing a beam of light having a predetermined limited extent in a vertical direction;
   (b) means selectively operable for limiting the extent of said beam of light in a horizontal direction transverse to said vertical direction so that said extent in said horizontal direction can be selectively varied; and
   (c) means for positioning a capillary having longitudinal and diametral directions so that the diametral direction of said capillary lies in said vertical direction of said beam of light end so that said beam of light passes through said capillary in a diametral direction thereof.

2. The adjustable aperture of claim 1, wherein said means for providing a beam of light having a limited extent in a vertical direction includes means for providing said beam of light so that said limited extent in said vertical direction is between about 10 and about 100 microns.

3. In combination, the adjustable-width aperture of claim 2, and a capillary having an inner diametral dimension, wherein said means for providing a beam of light having a limited extent in a vertical direction includes means for providing said beam of light so that said limited extent in a vertical direction is less than said inner diametral dimension of said capillary.

4. The adjustable-width aperture of claim 1, wherein said means selectively operable for limiting the dimension of a beam of light in a horizontal direction includes means selectively operable for limiting the dimension of said beam of light in a horizontal direction to between about 0.2 and about 2.0 mm.

5. The adjustable-width aperture of claim 1, wherein said means for providing a beam of light having a predetermined limited extent in a vertical direction comprises a body having an opening with a vertical dimension.

6. The adjustable-width aperture of claim 4, wherein said means selectively operable for limiting the extent of a beam of light in a horizontal direction comprises an element defining a plurality of slits of differing widthwise dimensions and means for selectively aligning any one of said slits with said beam of light so that the widthwise dimension of the aligned slit extends in said horizontal direction.

7. The adjustable-width aperture of claim 6, wherein said element defining a plurality of selectively interchangeable slits is rotatably mounted to said body.

8. The adjustable-width aperture of claim 5, wherein said body has a front face, and said opening extends to said front face, said opening further includes a horizontal dimension transverse to said vertical dimension, and said means for positioning a capillary comprises a groove on said front face, colinear with said horizontal dimension of said opening, in combination with means for retaining a capillary in said groove.

9. The adjustable-width aperture of claim 8, wherein said groove is beveled.

10. In combination, the aperture of claim 1 and an apparatus for sample analysis by capillary zone electrophoresis.

11. In combination, the aperture of claim 1, and an apparatus for sample analysis by high performance liquid chromatography.

12. A method for analyzing a sample comprising one or more compounds comprising the steps of subjecting said sample to capillary zone electrophoresis or high performance liquid chromatography within a capillary to thereby separate each said compound in said sample from other components of said sample within said capillary, and detecting said separated components in said capillary by providing a beam of light using an aperture as claimed in claim 1, directing said beam of light through said capillary and monitoring said beam after passage through said capillary.

* * * * *